United States Patent
Ramstad et al.

(10) Patent No.: US 7,235,163 B2
(45) Date of Patent: Jun. 26, 2007

(54) LOADING FEATURES FOR CHANNEL ARRAY

(75) Inventors: Paul O. Ramstad, San Jose, CA (US); Sean M. Desmond, San Carlos, CA (US); John Shigeura, deceased, late of Portola Valley, CA (US); by Janice G. Shigeura, legal representative, Portola Valley, CA (US); Richard T. Reel, Hayward, CA (US); Richard Morris, San Francisco, CA (US)

(73) Assignee: Applera Corporation, Foster City, CA (US)

( * ) Notice: Subject to any disclaimer, the term of this patent is extended or adjusted under 35 U.S.C. 154(b) by 492 days.

(21) Appl. No.: 10/661,231

(22) Filed: Sep. 12, 2003

(65) Prior Publication Data

US 2005/0056540 A1    Mar. 17, 2005

(51) Int. Cl.
- *G01N 27/447* (2006.01)
- *G01N 27/453* (2006.01)
- *G01N 30/02* (2006.01)
- *B01L 3/02* (2006.01)

(52) U.S. Cl. .................. 204/453; 204/604; 422/100; 422/70

(58) Field of Classification Search ............ 204/601, 204/604, 451, 453; 422/99, 100, 70
See application file for complete search history.

(56) References Cited

U.S. PATENT DOCUMENTS

| 4,911,807 | A | 3/1990 | Burd |
| 5,126,022 | A | 6/1992 | Soane |
| 5,164,064 | A | 11/1992 | Dill |
| 5,171,534 | A | 12/1992 | Smith |
| 5,213,766 | A | 5/1993 | Flesher |
| 5,858,188 | A | 1/1999 | Soane |
| 6,007,690 | A | 12/1999 | Nelson |
| 6,054,034 | A | 4/2000 | Soane |
| 6,143,252 | A | 11/2000 | Haxo |
| 6,375,817 | B1 * | 4/2002 | Taylor et al. ............... 204/453 |
| 6,479,301 | B1 * | 11/2002 | Balch et al. ................ 436/518 |
| 6,533,914 | B1 * | 3/2003 | Liu ............................ 204/601 |
| 6,939,452 | B2 * | 9/2005 | Foret et al. ................. 204/458 |
| 2002/0006359 | A1 | 1/2002 | Mathies |
| 2003/0062265 | A1 | 4/2003 | King |

FOREIGN PATENT DOCUMENTS

JP    2000233027 A    8/2000

OTHER PUBLICATIONS

Abstract of "Utilization of a computer-controlled laboratory workstation (Biomek 1000) in routine radioimmunoassay laboratory," Issac Hassan, Comput. Biol. Med. 1990;20(3):185-191.*

* cited by examiner

*Primary Examiner*—Alex Noguerola

(57) ABSTRACT

Apparatus and method for loading a channel device for electrophoretic separation including cilia which can be deflected into wells of a multi-well tray.

27 Claims, 9 Drawing Sheets

LOADING FEATURES FOR CHANNEL ARRAY

FIELD

The present teachings relate to devices and methods for loading samples from multi-well trays into channel devices.

INTRODUCTION

Electrophoresis separation channels can be configured into a channel device. A process for using a channel device can include: (i) depositing samples into corresponding sample wells, (ii) loading the samples into corresponding polymer-filled channels by hydrodynamic injection or electrokinetic injection, (iii) washing excess sample from the sample wells, and (iv) adding buffer for separation and analysis. These steps can involve transfer of the samples from the wells of a multi-well tray to the channel device. It can be desirable to provide flexible transfer from wells to a channel device that provides automated loading. The present teachings provide transfer by a plurality of discrete, elongated, flexible cilia. The pitch of the cilia can be set at a prescribed distance to facilitate registration with corresponding wells. For example, the pitch of the cilia at their sample-loading ends (i.e., the inlet-end to inlet-end spacing) can be configured to correspond to the spacing between wells on the multi-well tray.

SUMMARY

According to various embodiments, a channel device can include a substrate including a plurality of channels for electrophoretic separation, and a plurality of deflectable cilia in fluid communication with the plurality of channels, wherein the deflectable cilia are adapted to loading the plurality of channels from a multi-well tray. According to various embodiments, a system for electrophoretic separation can include a channel device including a substrate including of a plurality of channels and a plurality of deflectable cilia in fluid communication with the plurality of channels, a multi-well tray, and a support adapted to deflect the cilia to load the channels from the multi-well tray. According to various embodiments, a loading mechanism for a channel device can include a plurality of deflectable cilia adapted to fluidly communicate with a plurality of channels in a substrate for electrophoretic separation, wherein the deflectable cilia are adapted to loading the plurality of channels from a multi-well tray, and a support adapted to deflect the cilia to load the channels from the multi-well tray. According to various embodiments, a method for loading a channel device can include providing a multi-well tray, and deflecting at least one cilium from plurality of cilia adapted to fluidly communicate with a plurality of channels in the channel device. According to various embodiments, a method for electrophoretic separation can include providing a channel device that can include a substrate that can include a plurality of channels and a plurality of deflectable cilia in fluid communication with the plurality of channels, providing a multi-well tray, providing a loading mechanism to deflect the cilia to load the channels from the multi-well tray, deflecting at least one cilium to load at least one sample from the multi-well tray, deflecting the plurality of cilia into a buffer tray, and providing electric current for the electrophoretic separation.

It is to be understood that both the foregoing general description and the following description of various embodiments are exemplary and explanatory only and are not restrictive.

BRIEF DESCRIPTION OF THE DRAWINGS

The accompanying drawings, which are incorporated in and constitute a part of this specification, illustrate various embodiments. In the drawings.

DESCRIPTION OF VARIOUS EMBODIMENTS

Figure 1:
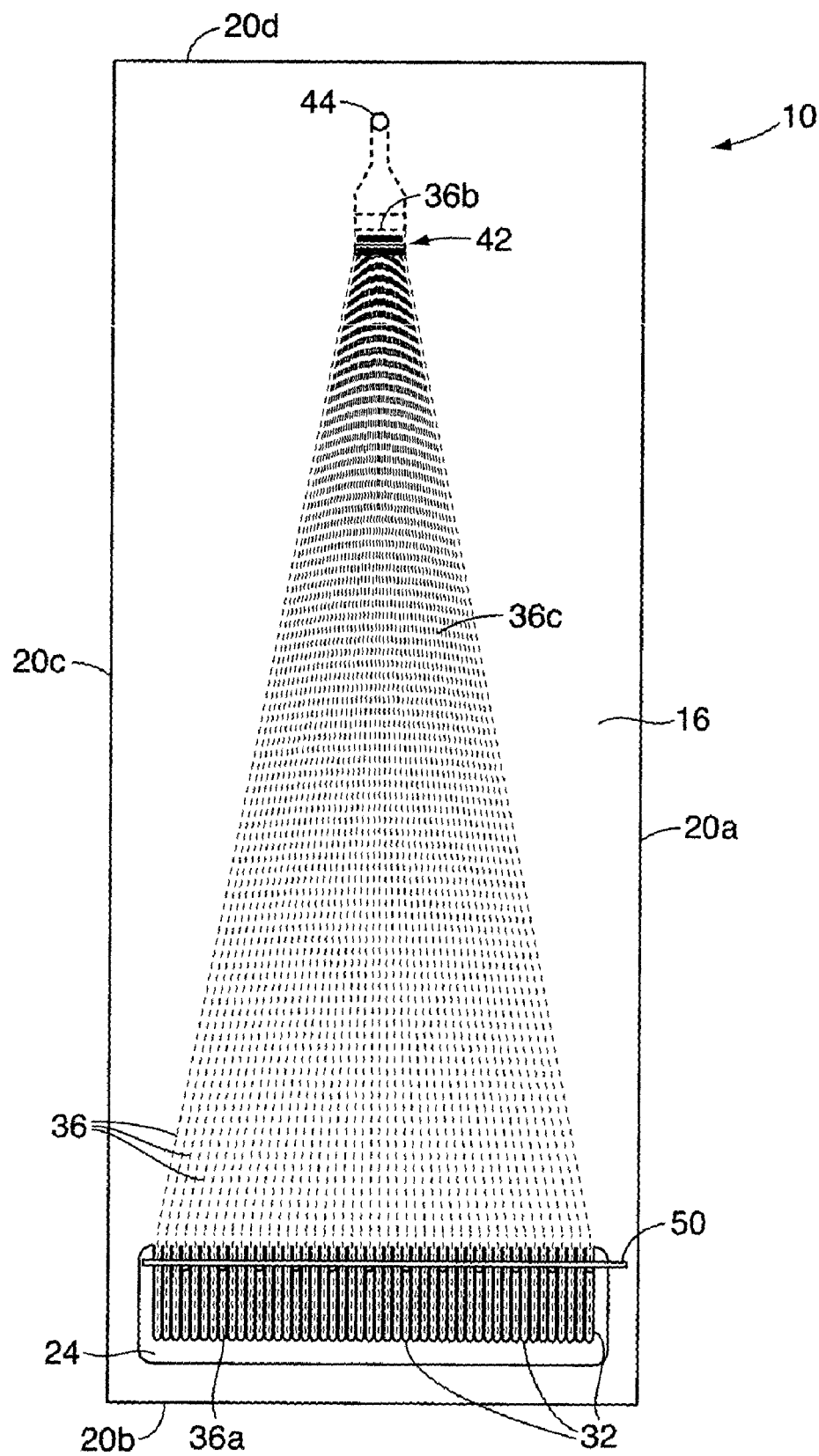
FIG. 1 illustrates a perspective view of various embodiments of a channel device.

Reference will now be made to various exemplary embodiments, examples of which are illustrated in the accompanying drawings. Wherever possible, the same reference numbers are used in the drawings and the description to refer to the same or like parts.

The term "channel" as used herein refers to an elongate, narrow passage or other structure (e.g., tubes, grooves, etc.) capable of supporting a volume of separation medium or separation matrix; e.g., such as is used in carrying out electrophoresis. The geometry of a channel can vary widely. For example, a channel can have a circular, oval, semi-circular, semi-oval, triangular, rectangular, square, or other cross-section, or a combination thereof.

The term "separation medium" or "separation matrix" as used herein refers to a medium in which an electrophoretic separation of sample components can take place. Separation media typically comprise several components, at least one of which can be a charge-carrying component, or electrolyte. The charge-carrying component can be part of a buffer system for maintaining the separation medium at a defined pH. Media for separating polynucleotides, proteins, or other biomolecules having different sizes but identical charge-frictional drag ratios in free solution, can further include a sieving component. Such sieving component can comprise a cross-linked polymer gel, e.g., cross-linked polyacrylamide or agarose (see, e.g., Sambrook), or a polymer solution, e.g., a solution of polyacrylamide, hydroxyethyl cellulose, and the like.

The term "channel device" as used herein refers to a substrate, such as a plate, wafer, slide, chip, disc, or the like, including one or more channels. As used herein, a "channel device" does not consist of a plurality of discrete (from one end to the other), elongate, capillary tubes. Channel devices can include multiple channels, for example configured in an array, formed in a rigid substrate, such as glass or plastic.

One or more wells can be provided for fluid communication with the channels for receiving samples, other reagents, and/or buffer. One or more waste wells can be provided. Wells can be formed at fixed positions in the substrate.

The term "cilia" as used herein refers to a plurality of discrete, elongated, flexible finger-like projections for loading channels. Cilia can be, for example, capillary tubes. The pitch of the capillary tubes can be set at an integral fraction to facilitate registration with corresponding wells. For example, the pitch of the capillary tubes at their sample-loading ends (i.e., the inlet-end to inlet-end spacing) can be set at an integral fraction of 9 mm (e.g., 9 mm, 9/2 mm, 9/3 mm, etc.) in order to facilitate registration of the capillary tube inlets with sample wells of a standard-format multi-well tray. The cilia can be smaller in diameter than the well and configured to be deflected into the well and reach the liquid sample. The cilia can be configured to pierce through a thin plastic cover on the multi-well tray. The cilia can have a rigidity configured to slide through septa over each well of the multi-well tray, such as the one described in U.S. Pat. No. 5,916,526.

The term "deflect" and grammatical variations thereof such as "deflectable", as used herein refer to feature of the cilia to bend, flex, change direction, turn, or any movement controlled by loading mechanism to load the sample from the multi-well tray to the channels of the channel device. The term "loading mechanism" as used herein refers to the cilia and the means for deflecting the cilia whether external to the structure of the cilia, e.g., a support, or internal to the structure of the cilia, e.g., tendon element, including any components for the automation of such. The loading mechanism can be an active mechanism providing control of individual cilia or sets of cilia. Active mechanism can be external to the structure of the cilia, e.g., a solenoid, or internal to the structure of the cilia, e.g., coil wrapped around each cilium.

The term "multi-well tray" and grammatical variations thereof, as used herein refers to any array for containing samples. The term "well" as used herein refers a member of the array. Multi-well trays include a standard-format, 96-well plate having an 8×12 array of wells which have regularly spaced wells 9 mm apart. Multi-well trays include microtiter plates, microplates, tubes arranged in racks, and other closed end containers. Multi-well trays include microslides, microcards, etc. Multi-well trays can be configured to include wells in rows and columns, rings, random, or any design that can be programmed into the CPU to position the cilia and/or tray for loading from the arrangement of wells. Multi-well trays can have a rectilinear shape, a circular disk-shape, and the tray surface of the wells can be substantially flat or curved. A multi-well tray can be formed integrally with a plate or tray, arranged in a regular rectangular array spaced an integral fraction center-to-center. A multi-well tray can be formed as discrete wells interconnected by plastic webbing, or supported in an appropriate holder, to provide an array. A multi-well tray can be in the form of strips. For example, a plurality of wells could be disposed in a row with adjacent wells connected to one another by any suitable means, e.g., frangible plastic webs. A plurality of strips could then be arranged side-by-side within a frame designed to hold such strips. For example, twelve 8-well strips could be placed side-by-side in a rectangular frame to form a 96-well array. A multi-well tray can be formed as tubes removably positioned within a respective opening formed in a support plate or rack. For example, a tray could be provided with a 12×8 array of circular openings in which cylindrical wells, or tubes, are received and held, in a fashion similar to test-tubes held in a conventional test-tube rack.

According to various embodiments, the present teachings provide, among their various aspects, channel devices that include a plurality of channels in a substrate attached to an array of cilia, which provide sample-loading ends for the channels. A channel device can include a monolithic structure, including one or more channels therein. For example, such monolithic structures can comprise a single piece of material, such as a unitary plate of glass or plastic. In various embodiments, such monolithic structures comprise a laminate structure.

According to various embodiments, channels can be formed in a generally planar substrate including of one or more film materials. Film materials useful in constructing channel devices can include polymethylmethacrylate (PMMA)-acrylic; Zeonor™ cyclo-olefin; and other suitable materials exhibiting one or more of: low permeability, low background fluorescence, chemical inertness, electrical insulation, flame retardance, and/or high clarity with a low index of refraction.

According to various embodiments, channel devices of the present teachings can be formed in or on a substrate by fabrication techniques known in the art, including but not limited to, e.g., photolithographical and/or wet-chemical etching procedures, laser ablation, electroforming, microcontact printing, microstamping, micromolding, microcasting, micromachining, microlamination, engraving, and/or embossing techniques. For example, Backhouse et al., DNA sequencing in a monolithic microchannel device, Electrophoresis 2000, 21, 150–156; Dolnik et al., Capillary electrophoresis on microchip, Electrophoresis 2000, 21, 41–54; Woolley et al., Ultra-high-speed DNA fragment separations using microfabricated capillary array electrophoresis chips, Proc. Natl. Acad. Sci., vol. 91, pp. 11348–11352, November 1994; and Madou, Fundamentals of Microfabrication, CRC Press, Boca Raton, Fla. (1997) (each of which is incorporated herein by reference) discuss certain microfabrication techniques that the skilled artisan can employ in making channel devices.

A channel device, as contemplated by various embodiments herein, can include one or more channels, e.g., at least 2, 4, 8, 16, 32, 48, 96, 384, or more channels.

According to various embodiments, FIG. 1 illustrates a channel device including the present teachings. Channel device 10 includes substrate 16 with sides 20a–20d. Side 20b is the loading side, side 20d is the detection side, and sides 20a and 20c form the plane of electrophoretic separation. The detection side 20d of substrate 16 includes detection zone 42 which connects with buffer reservoir 44 in fluid contact with channel device 10 through the conduit shown in ghost lines. Substrate 16 includes a plurality of channels 36. The outlet ends 36b of channels 36 are in fluid contact with detection zone 42. Channels 36 can include an inlet end 36a, an outlet end 36b, and an elongate lumen 36c extending between and providing fluid communication between the inlet ends 36a and outlet ends 36b. FIG. 1 illustrates the relative position of support 50 with channel device 10.

Figure 1A:
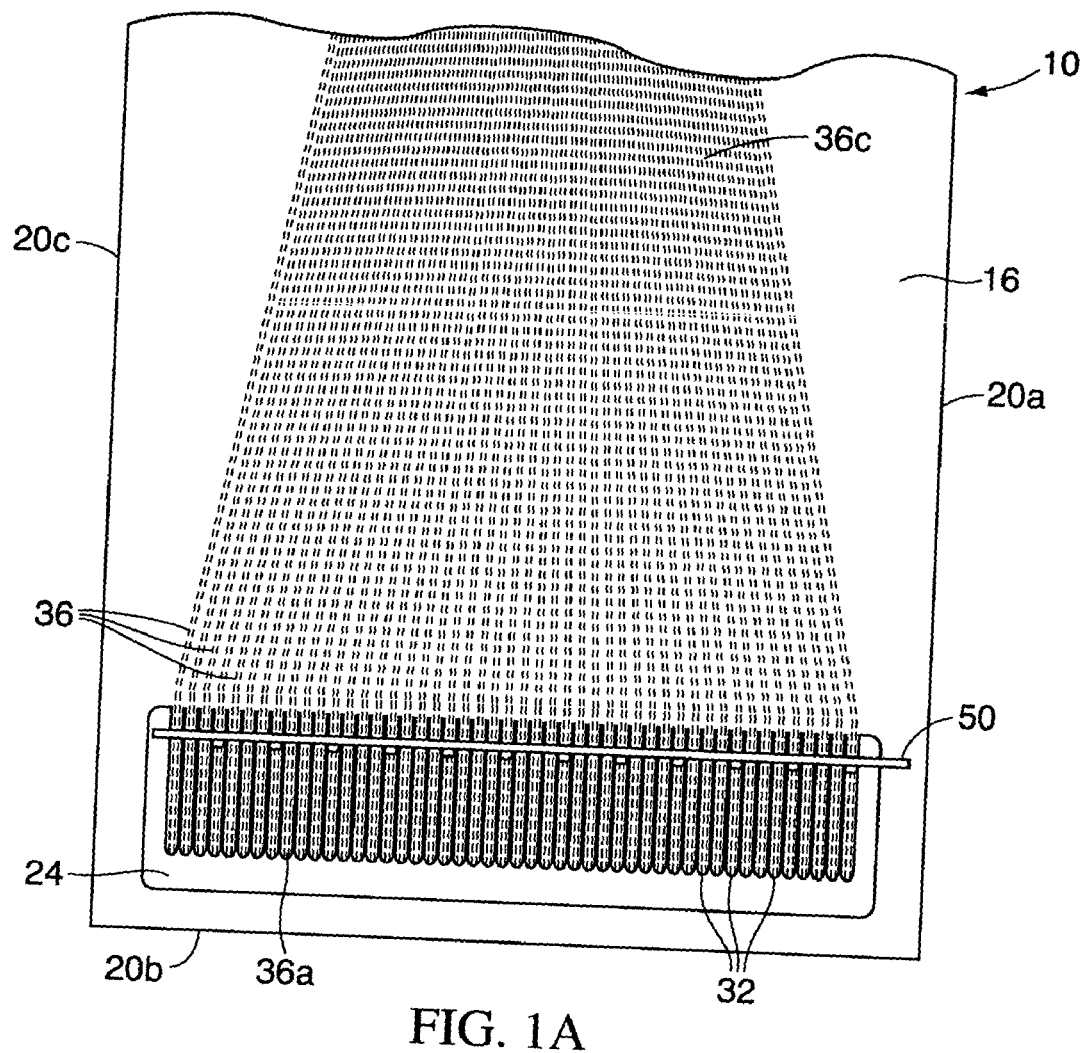
FIG. 1A illustrates a magnified view of a portion of the channel device illustrated in FIG. 1.

According to various embodiments, FIG. 1A illustrates a magnified view of the loading side 20b of substrate 16 of the channel device 10 illustrated in FIG. 1. A portion of each of the channels 36, including each channel's inlet end 36a and at least a portion of its lumen 36c, are formed by cilia 32. The cilia 32 can be positioned in opening 24 in substrate 16.

Those skilled in the art will recognize that a channel device according to the present teachings can further include, or be used in combination with, additional components generally employed with electrophoretic apparatus. For example, although not shown, a first lead wire can connect a power source with a first electrode disposed for electrical communication with the inlet ends of the separation channels; and a second lead wire can connect the power source with a second electrode disposed for electrical communication with the outlet ends of the separation channels. In operation, a voltage can be applied between the first and second electrodes, and thereby along the channels, such that a sample zone is transported from the inlet ends, toward the outlet ends of the channels, and through the detection zone. A light source (e.g., a laser) can be configured to direct an excitation beam along the detection zone to excite fluorescent markers attached to species of interest (e.g., DNA fragments) as they pass therethrough, and a detector (e.g., CCD) can be disposed along an emission beam path to detect emissions from such markers to thereby identify the species of interest. Those skilled in the art will appreciate that other arrangements for establishing an electrical field across the device and detecting species of interest can be employed, and that the just-discussed arrangement is by way of example only.

According to various embodiments, the pitch (channel-to-channel spacing) between adjacent inlet ends 36a of channels 36 formed by cilia 32 can be 2.25 mm. In other various embodiments, the pitch is 1.125 mm. In still further various embodiments, the pitch is 4.5 mm. It will be appreciated that the invention is not limited to any particular pitch, and that any other desired channel-to-channel spacing can be employed.

According to various embodiments, cilia 32 can include features designed to facilitate hydrodynamic and/or electrokinetic injection of a small volume (approximately 1 µL or less) of sample. In some embodiments, for example, such features are like the fountain-pen nib type probes used to spot-transfer liquid samples from tubes to slides.

Figure 2:
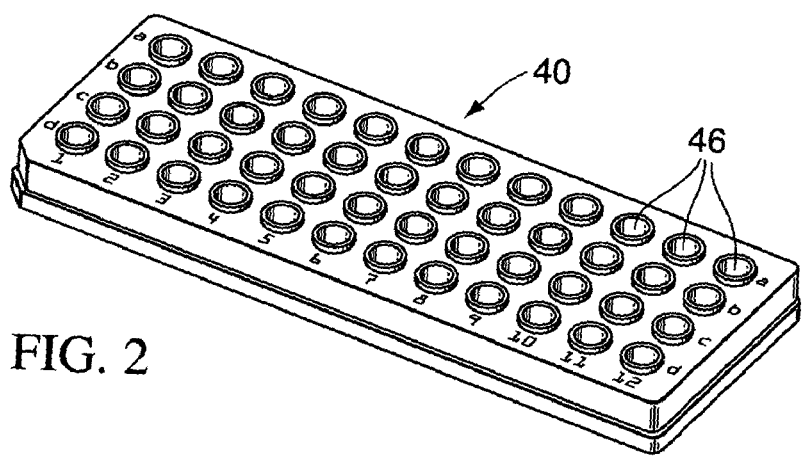
FIG. 2 illustrates various embodiments of a multi-well tray.

As described more fully below, each of the cilia 32 can be inserted into a multi-well tray 40 in order to load a sample onto its channel 36. FIG. 2 illustrates multi-well tray 40 having a 4×12 array of wells 46 (i.e., 48 wells, comprising rows "a–d" and columns "1–12"). Although the illustrated embodiment shows a 48-well arrangement, the invention contemplates any other desired number of wells (e.g., 12, 24, 48, 384, 1536, etc.) disposed in any suitable configuration.

According to various embodiments, FIGS. 3A–3F illustrate positioning the channel device 10 above the multi-well tray 40, such that the plane of the channel device 10, x-y plane, can be substantially parallel to the plane of the upper surface of the tray 40, also in x-y plane. In such an embodiment, the substantially parallel position of the channel device 10 to tray 40 provides loading by positioning in the x-y plane without any z-axis movement. According to various embodiments, the plane of the channel device 10 can instead be angled with respect to the plane of the tray, i.e. at an angle to the x-y plane. In such an embodiment, the position of channel device 10 relative to tray 40 provides loading by positioning in x,y,z directions.

According to various embodiments, tray 40 can be stationary with channel device 10 positioned for loading cilia 32. According to various embodiments, channel device 10 can be stationary with tray 40 positioned for loading cilia 32. According to various embodiments, both tray 40 and channel device 10 can be positioned for loading cilia 32.

According to various embodiments, support 50 can be positioned above the channel device 10. The support 50 can include a plurality of spaced-apart posts 52 extending from the lower side or edge of support 50 facing substrate 10. According to various embodiments, each post 52 includes a foot 54 at a lower end of the post 52. Foot 54 can provide a guiding surface to deflect cilia 32 into wells 46. According to various embodiments, support 50 can be positioned by movement in the x,y,z-axes to deflect cilia 32 with posts 52.

Figure 5:
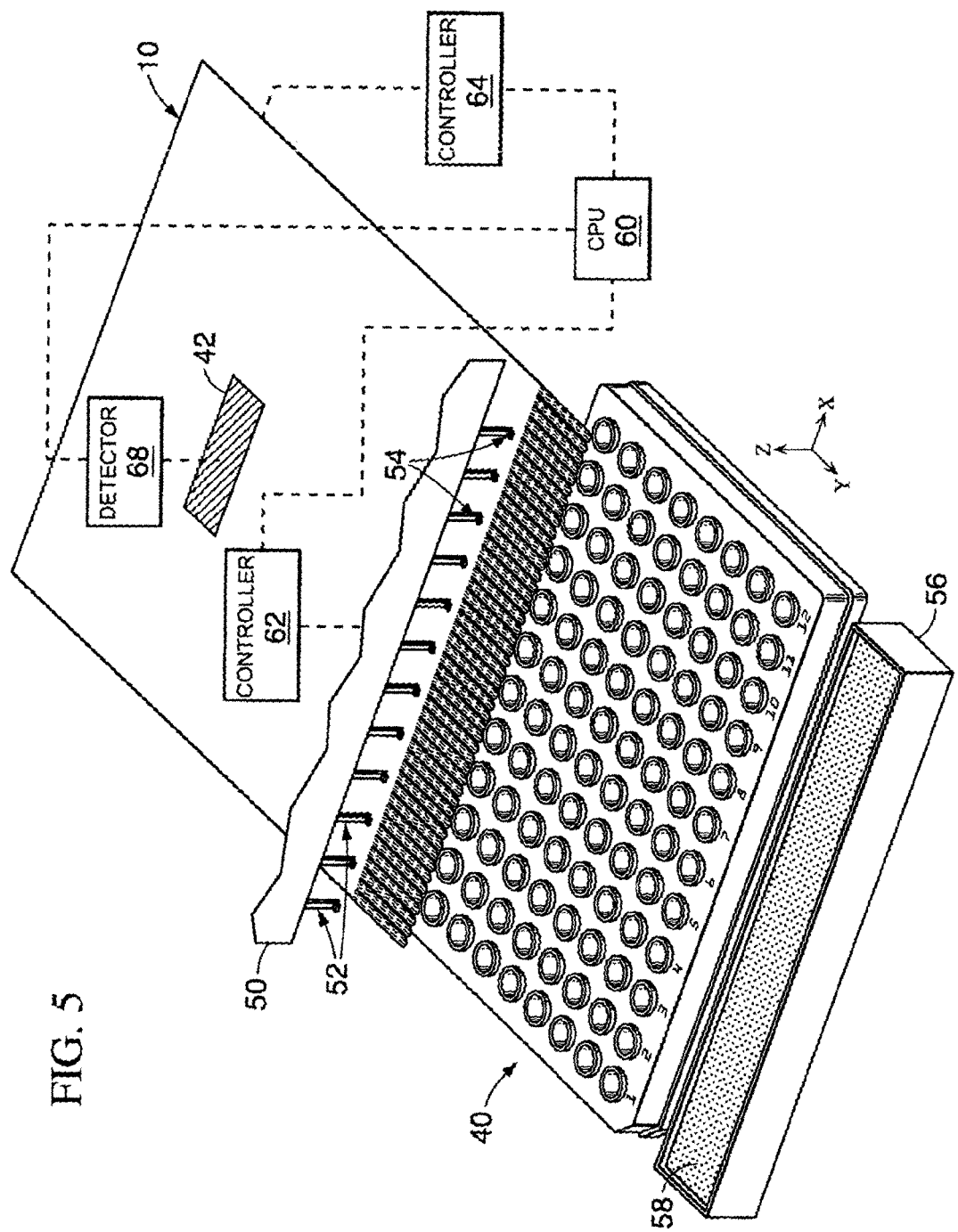
FIG. 5 illustrates a diagrammatical view of various embodiments of a system for loading a channel device and detecting the separation.

According to various embodiments, positioning of support 50 can be provided in a substantially automated fashion, e.g., using any suitable moving mechanism; although it will be appreciated that manual and/or hybrid arrangements can be used. FIG. 5 illustrates support 50 adapted for x,y,z-positioning by way of controller 62, under the direction of CPU 60. The performance envelope of the controller 62 permits movement of the support 50 toward, away from, across, and/or beyond the channel device 10. The CPU 60 can be programmed, by conventional techniques, to move the support 50 to a specific location relative to the channel device 10.

According to various embodiments, controller 62 includes a z-motion actuator coupled to an x,y-shifting assembly. The z-motion actuator can be operatively connected to the support 50 for moving it along the z direction, toward and away from channel device 10. The z-motion actuator can be, for example, a hydraulic, pneumatic, or motor-driven actuator. Several assemblies that can be adapted for use herein are disclosed, for example, in U.S. Pat. Nos. 3,164,304; 3,329, 964; 3,334,354; 5,306,510; 5,443,791; 5,525,515; 5,551, 487; 5,601,980; and 5,807,522; each of which is expressly incorporated herein by reference. The x,y-shifting assembly, to which the z-motion actuator is coupled, is adapted to move the z-motion actuator linearly or in an x-y plane to locate the actuator at a selected location over cilia 32 of the channel device 10. Exemplary automated devices useful for x,y-shifting include, for example, robots with electronically controlled linked or crossed movable arms, such as a SCARA, gantry and Cartesian robots. One embodiment employs a motorized x,y-carriage or rail arrangement. In another embodiment, an arm that supports the z-motion actuator is threadedly mounted on a worm screw that can be driven (rotated) in a desired direction by a motor (e.g., stepper), as directed by the control unit. It is understood, of course, that any other robotic mechanism could be used in accordance with the present invention so long as it can accomplish substantially the same purpose(s) and secure substantially the same result. Several exemplary x,y-shifting assemblies which can be adapted for use herein are disclosed, for example, in U.S. Pat. Nos. 5,443,791; 5,551,487; 5,306,510; and 5,587,522; each of which is expressly incorporated herein by reference.

According to various embodiments, as illustrated in FIG. 5, the channel device 10 can be positioned by controller 64 which can include an x,y-shifting assembly and/or a z-motion actuator. The channel device 10 can be positioned in conjunction with support 50 for loading cilia 32 from the wells 46 in tray 40. The channel device can be positioned in conjunction with buffer tray 56 so that support 50 can submerge cilia 32 into buffer 58 which can allow channel device 10 to conduct electrophoresis. CPU 60 can direct controller 64. According to various embodiments, CPU 60 can direct controllers 62 and 64 to designate which cilia 32 is loaded from each well 46. According to various embodiments, CPU 60 can correlate the images providing electrophoretic separation information collected by detector 68 from detection zone 42 to the sample in each channel 36 as it exits the outlet ends 36b in detection zone 42. The CPU 60 can thereby determine which image is associated with the sample from each well 46. According to various embodiments, controllers can position the tray 40 in the x,y,z,-direction, while maintaining the channel device 10 stationary.

Figure 3A:
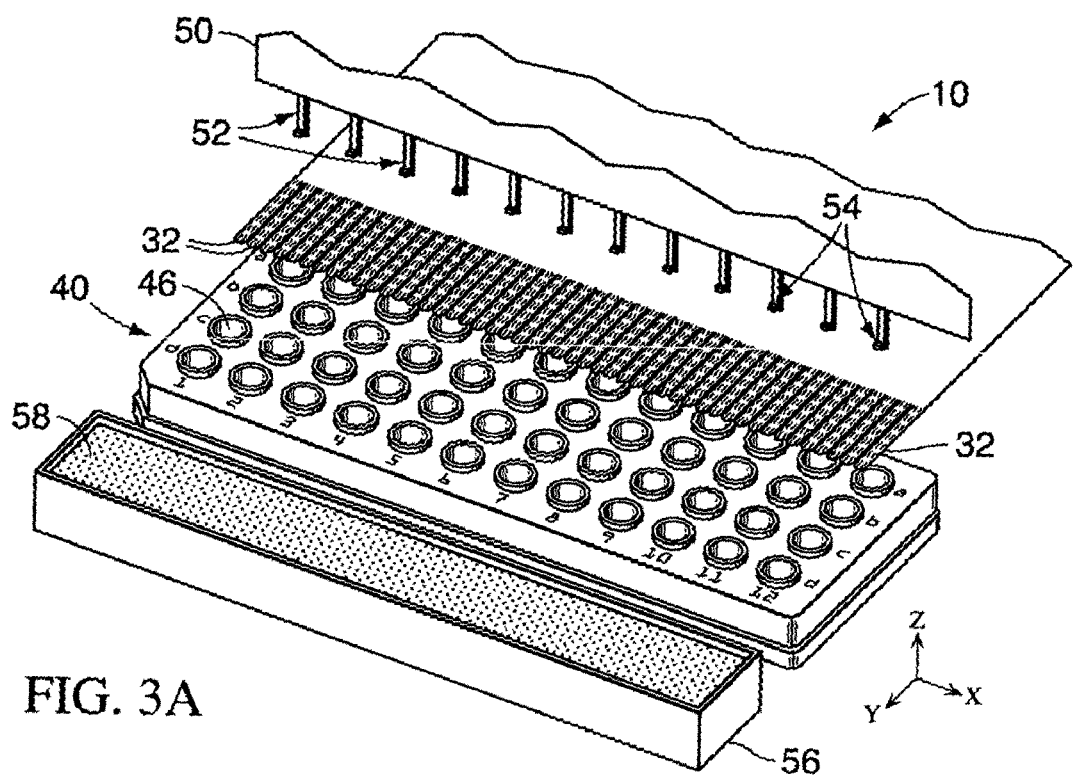
FIGS. 3A–3F illustrate diagrammatically various embodiments of loading the channel device from multi-well tray and buffer tray.
Figure 3B:
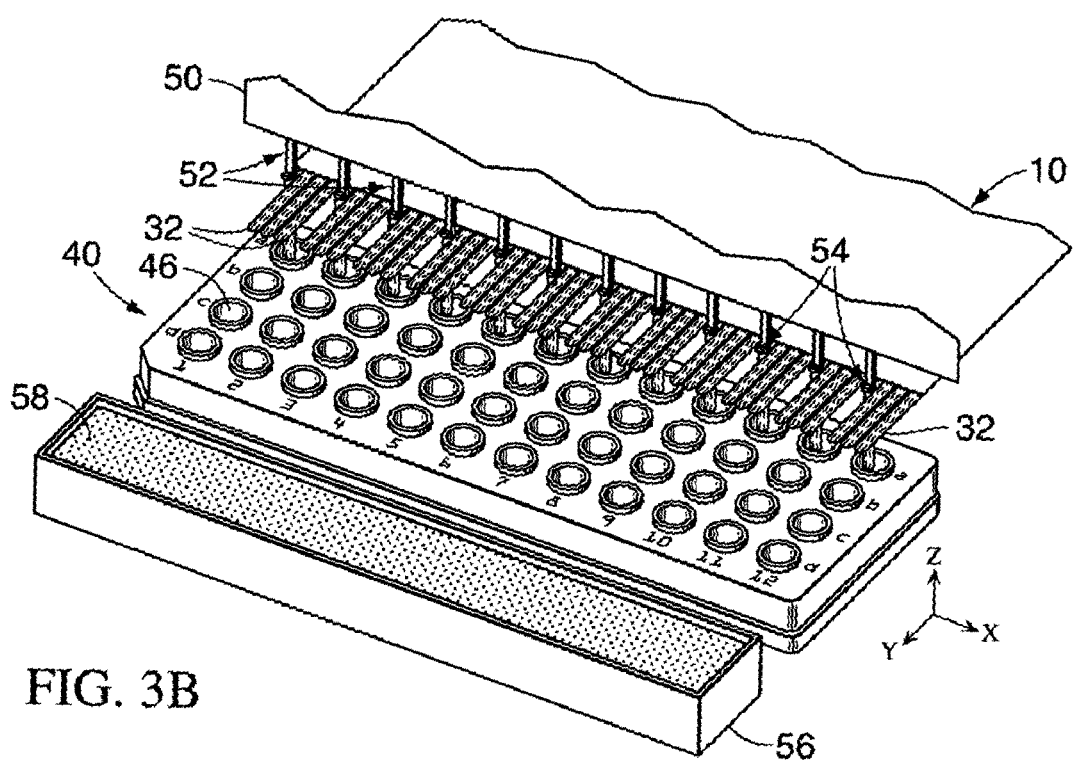
Figure 3C:
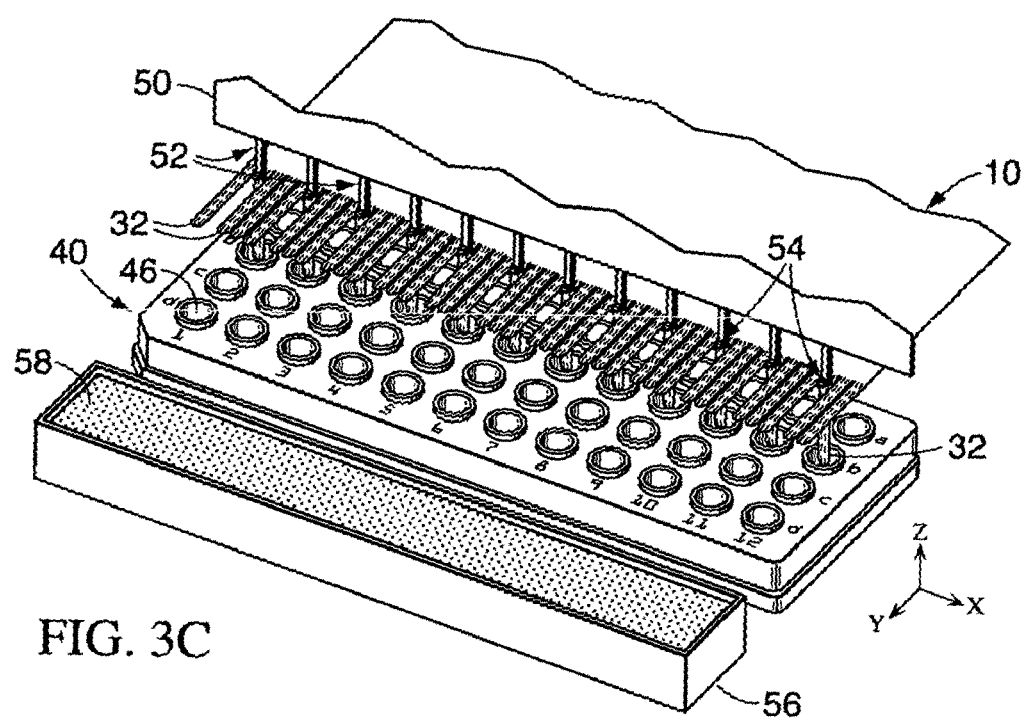
Figure 3D:
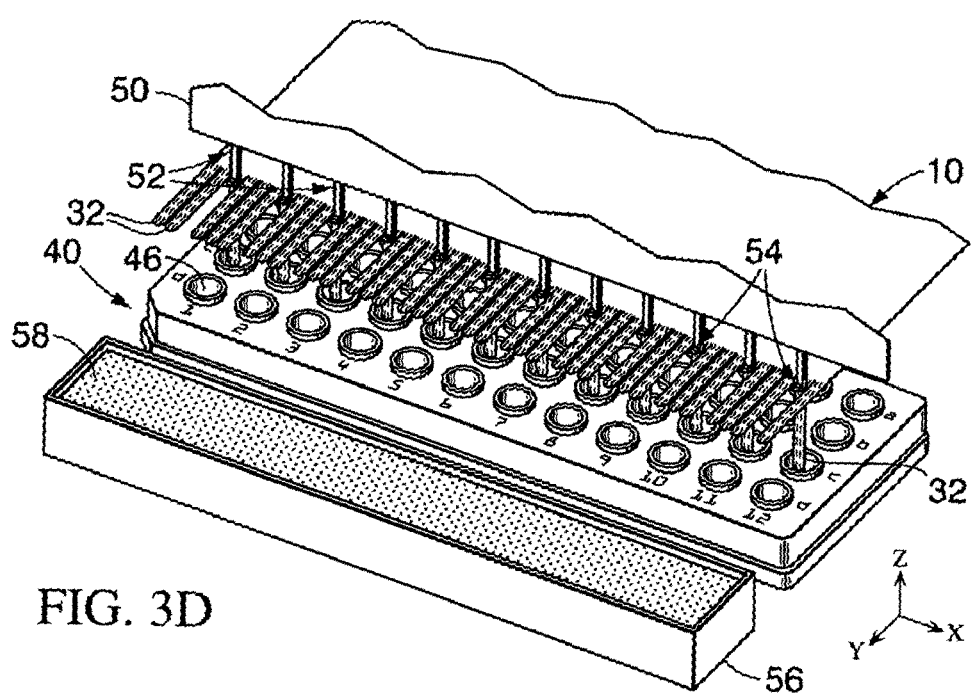
Figure 3E:
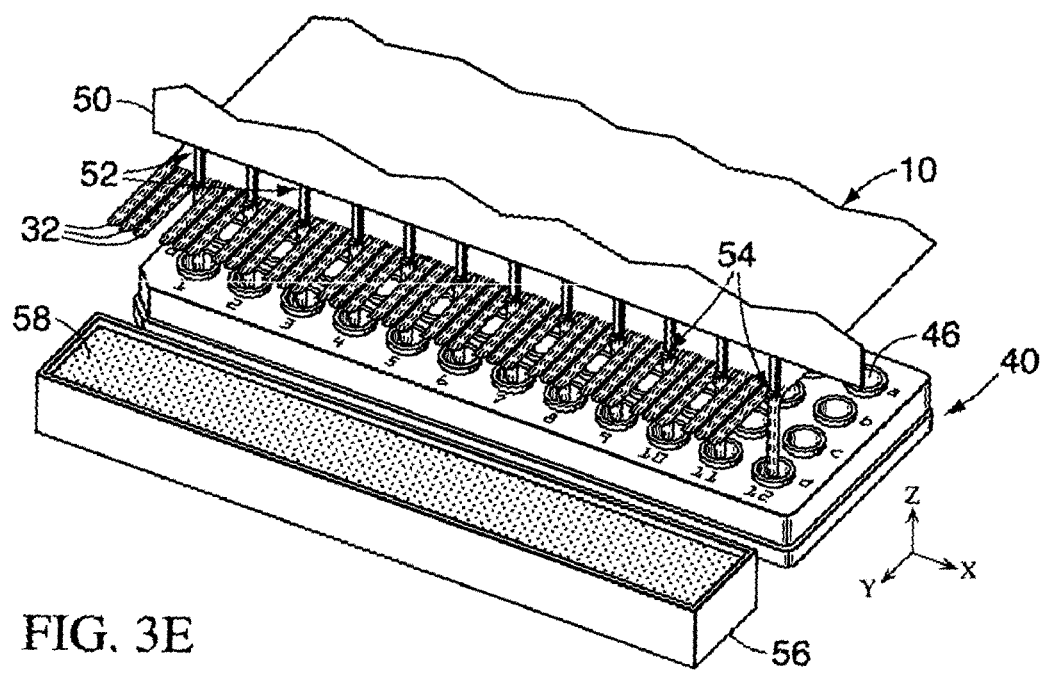
Figure 3F:
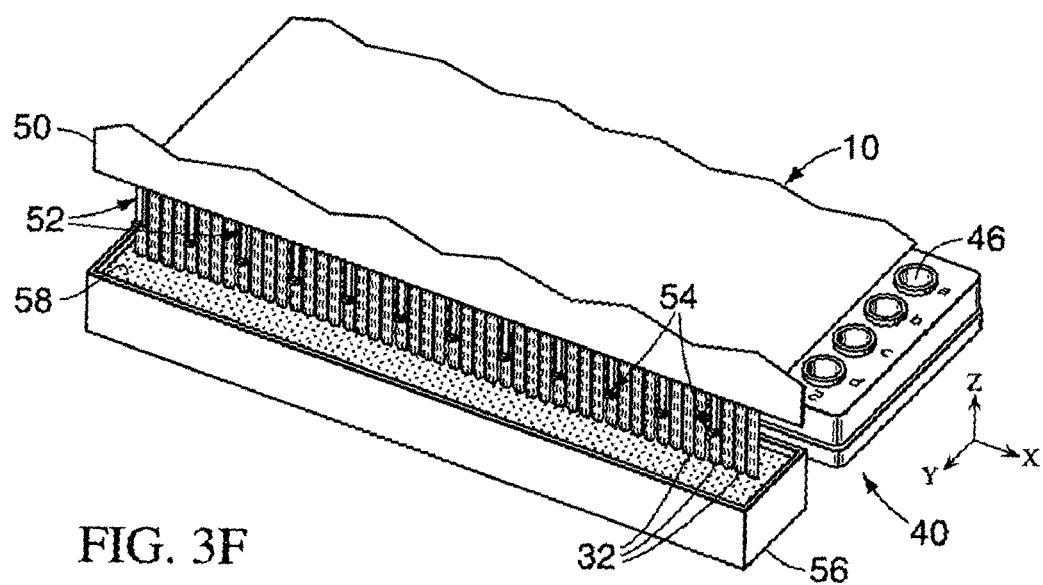

According to various embodiments, as illustrated in FIGS. 3A–3F a tray 40 can be positioned below the horizontal array cilia 32. A support 50 including twelve posts 52 can approach the cilia 32 in the z-direction, deflecting twelve of the cilia 32 into the wells 46 of tray 40 upon making contact therewith, thus enabling them to extract some of the contents of the individual wells 46. FIGS. 4A–4F correspond to FIGS. 3A–3F, respectively, showing the position of the channel device 10 relative to the tray 40 (FIGS. 3A and 4A), the sequential deflection of cilia 32 to load sample 70 from wells 46 (FIGS. 3B–3D and 4B–4D), and the submerging of all cilia 32 into buffer 58 in buffer tray 56 (FIGS. 3F and 4F). By raising support 50 in the z-direction, cilia 32 can return to a horizontal state, out of the sample-plate reservoirs.

Figure 4A:
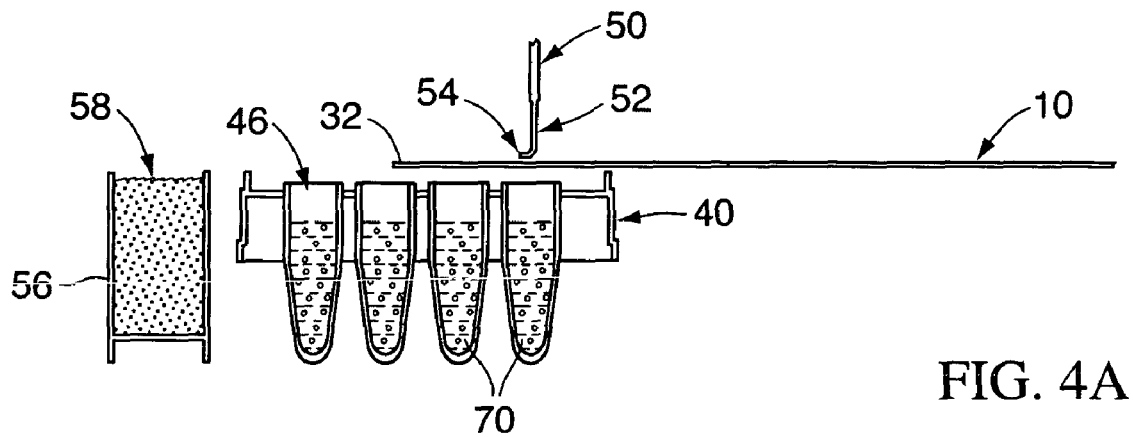
FIGS. 4A–4F illustrate a cross-sectional view of various embodiments of loading the channel device from multi-well tray and buffer tray.
Figure 4B:
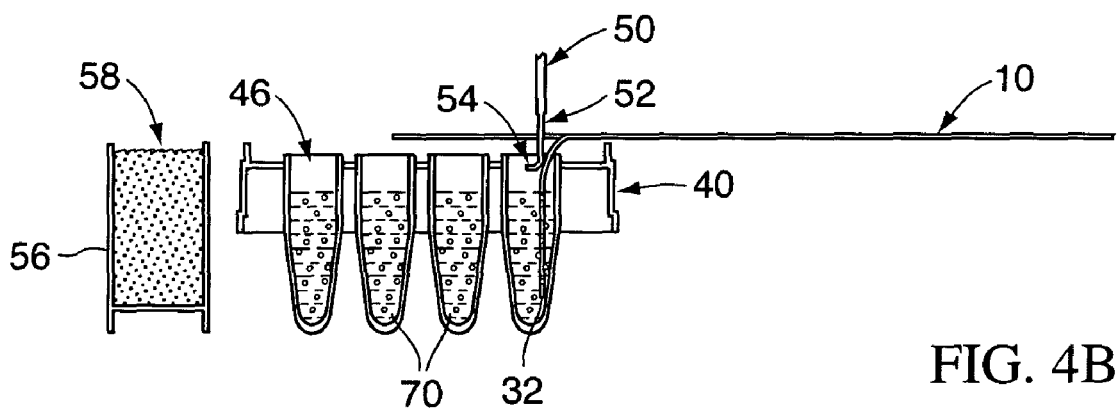
Figure 4C:
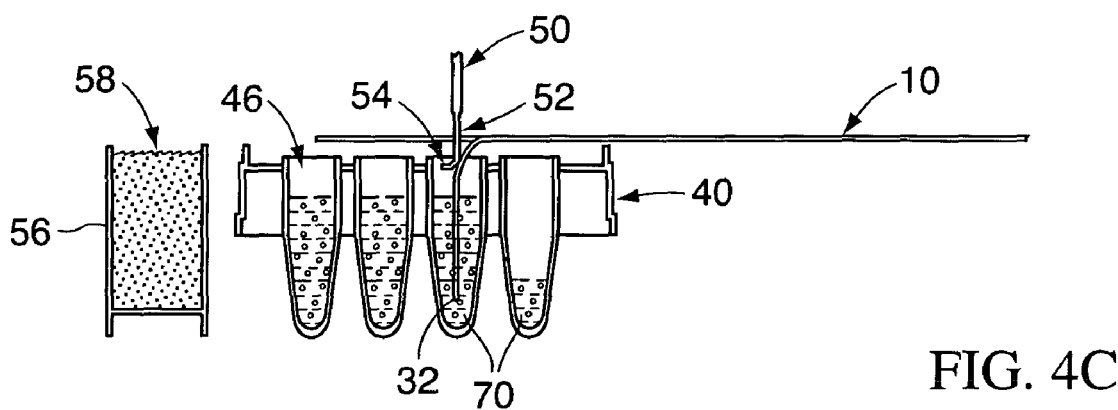
Figure 4D:
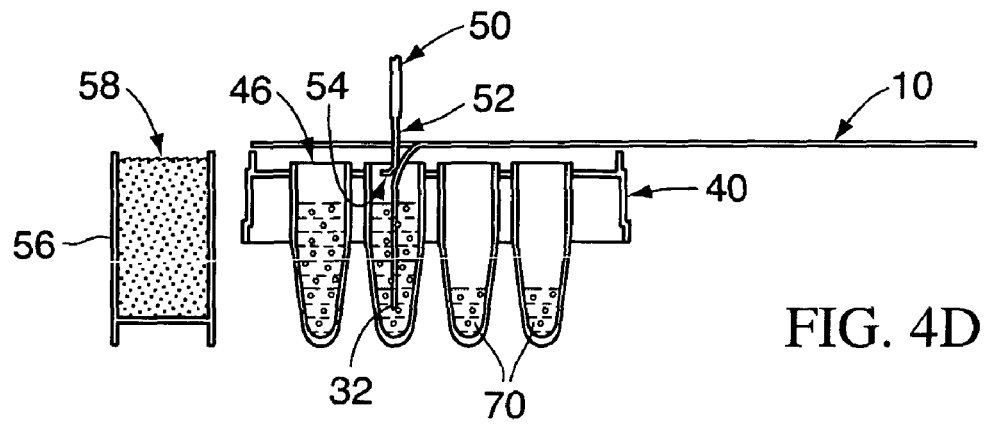
Figure 4E:
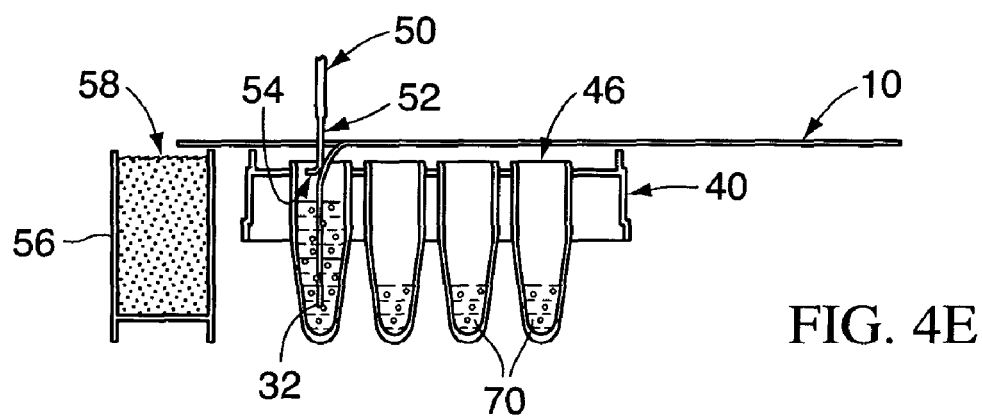
Figure 4F:
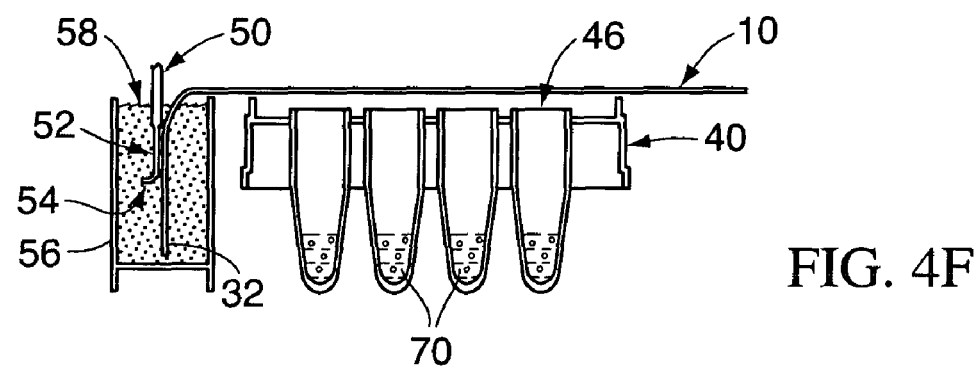

According to various embodiments, FIGS. 3B and 4B illustrates the deflection of the first set of twelve cilia 32 by posts 52 into the first row of wells 46 and the filling with sample 70. FIGS. 3C and 4C illustrates the deflection of the second set of twelve cilia 32 by posts 52 into the second row of wells 46 and the filling with sample 70. According to various embodiments, the second set of twelve cilia 32 can be adjacent to the first set of twelve cilia 32. FIGS. 3D and 4D illustrates the deflection of the third set of twelve cilia 32 by posts 52 into the third row of wells 46 and the filling with sample 70. FIGS. 3E and 4E illustrated the deflection of the fourth set of twelve cilia 32 by posts 52 into the fourth row of wells 46 and the filling with sample 70. According to various embodiments, any number of cilia 32 can be loaded from any number of wells 46 with sample 70, whether they are loaded a whole row at a time, individually, or any combination thereof. According to various embodiments, the arrangement of posts 52 on support 50 can be configured to provide desired loading into channels 36. According to various embodiments, the deflection of cilia 32 by posts 52 can be conducted to provide desired loading into channels 36.

According to various embodiments, an indexing mechanism can position the tray 40 so that wells 46 align with cilia 32 for loading channels 36 via the deflection of cilia 32 by posts 52 on support 50. According to various embodiments, a wash tray can be provided to rinse cilia 32 to remove excess sample 70. According to various embodiments, a buffer tray 56 can be provided to submerge cilia 32 to conduct electrophoresis in channels 36. According to various embodiments, support 50 can deflect all cilia 32 by moving along the z-axis beyond the extent of posts 52. Such deflection can provide substantially simultaneous submergence cilia 32 in a wash tray or buffer tray 56.

According to various embodiments, preformed cilia substantially perpendicular to the horizontal array can be selectively straightened to remove them from sample wells or reservoirs. Retraction of the straightening device would allow the cilia to spring back, returning them to the preformed state.

According to various embodiments, extended cilia 32 together with the indexing mechanism can be used to stir or mix samples 70 within their respective wells, or to stir, or mix fluids in other reservoirs, or as a washing means for the cilia themselves.

According to various embodiments, the inclusion of features, such as alignment grooves, on the channel device and/or cilia that can engage the flexing and dipping mechanism would allow for more direct control of each cilium, and perhaps be more tolerant of plate-to-actuator misalignment. The tray and/or cilia can include alignment features corresponding to the mechanism used to aid in the determination and registration of loading and/or detection of the channel device.

According to various embodiments, the cilia can include shape-memory alloy material known in the art of memory metal. For example, bimetallic actuators constructed of shape-memory alloy material can be configured as a flexing and dipping mechanism to deflect the cilia into wells. Shape-memory alloys are configured to change shape or size when subjected to the appropriate stimulus. Shape-memory materials that can change back have two-way shape memory. Shape-memory materials include nickel-titanium alloys and copper-base alloys such as CuZnAl and CuAlNi. According to various embodiments, the cilia can include tendon-like elements that flex the hinge joint, individually or in sets.

According to various embodiments, the channel device and cilia can include fluidic ports and circuitry that enable sample concentration, dilution, mixing, exchange, pipetting, washing, and/or sheath flow. These ports can also be coupled to fluidic manifolds within the indexing mechanism, or base instrument.

According to various embodiments, plated electrodes of gold, platinum, stainless steel or other suitable electrically conductive material deposited on, or integral to the channel device and cilia could enable liquid-level detection, temperature measurement, heating, PCR, electromagnetic oscillation or sample pull-out, electro-flow, and/or electrokinetic injection of the samples into the channels. These electrodes can include circuitry and components that mate with electronics included as part of the CPU, or base instrument. For example, the support illustrated in FIGS. 3A–3F can be a negatively charged electrical conductor contacting electrodes plated on the top surface of the cilia, and the detection zone of the channel device can be grounded to provide electrokinetic injection and electrophoretic separation.

Figure 6:
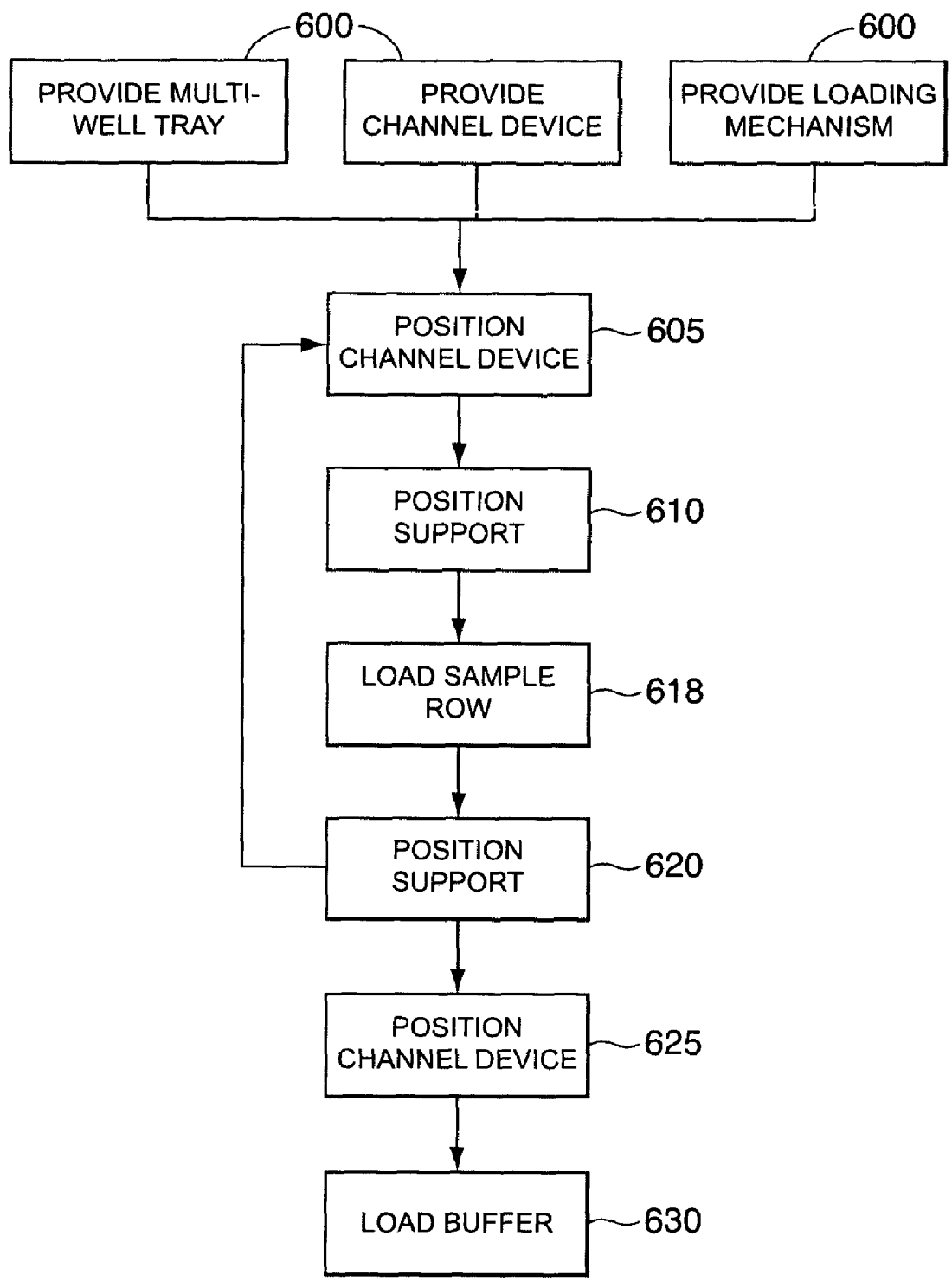
FIG. 6 illustrates a flow chart of various embodiments of a method of loading the channel device from multi-well tray and buffer tray.

According to various embodiments, FIG. 6 illustrate a method for loading the channel device. Step 600 can include providing a multi-well tray. Step 600 can include providing a channel device. Step 600 can include providing a loading mechanism which can include cilia and a support. Step 605 can include positioning the channel device. Step 605 can include positioning the multi-well tray (not shown). Step 610 can include positioning the support to deflect the desired cilia. Step 618 can include loading the sample into the cilia from a row. Step 620 can include positioning the support to permit the cilia to return to their original position. Repeating steps 605, 610, 618, and 620 provides loading of cilia from each row of the multi-well tray. Step 625 can include positioning the channel device over a wash tray or buffer tray. Step 625 can include washing excess sample from the cilia (not shown) by deflecting all the cilia. Step 630 can include loading buffer by deflecting all the cilia into a buffer tray. According to various embodiments, the method can include intermediary steps such as electrokinetic injection and subsequent steps such as conducting electrophoretic separation.

According to various embodiments, the number of wells in the multi-well tray can correspond to individual channels in the channel device. According to various embodiments, the channel device can have fewer channels than wells in the multi-well tray. The CPU can calculate timing for serial injections by subsequent deflections of the same cilium into the multi-well tray with intermediate deflections into a wash tray.

According to various embodiments, the cilia can include a tendon element to control the deflection. The tendon element can provide mechanism control over the deflection. According to various embodiments, the cilia can be resilient after deflection to return to their initial position, e.g., whether parallel or perpendicular to the tray. According to various embodiments, the cilia can be deformable, i.e., non-resilient and remain in a second position, e.g., curved as opposed to straight.

According to various embodiments, the present teachings can provide an apparatus for transferring samples from a multi-well plate to the channels of a channel device for use in DNA analysis. According to various embodiments, the present teachings can provide a method to automate process as readily performed as direct loading into cilia from a multi-well tray. According to various embodiments, the present teachings can provide a system for reducing fluidic and robotic requirements, and optimizing its application in DNA separation and analysis, either as a single use consumable, or for multi-use applications.

According to various embodiments, the present teachings can provide an apparatus for loading a separate channel device. The loading mechanism, i.e., cilia and support, can be configured into an interface between a multi-well tray and a channel device. According to various embodiments, the present teachings can provide the assembly of a channel device by integrating the loading mechanism into the channel. According to various embodiments, the present teachings can provide handling and alignment associated with methods of transfer of samples from a multi-well tray to a channel device. According to various embodiments, the present teachings can reduce the fluidic and robotic components in a loading mechanism. According to various embodiments, the present teachings can increase the utility of channel devices in DNA separation and analysis, either as a single use consumable, or for multi-use applications.

According to various embodiments, the loading mechanism can be incorporated into the cilia themselves or corresponding to each cilium, such that it can be configured to individually activate each cilium. The term "active mechanism" as used herein refers to a mechanism to deflect the cilia incorporated into the cilia or corresponding to each cilium, such as individual actuators. The cilia can be directed to deflect by using an active mechanism adapted to bend a set cilia or each cilium individually. According to various embodiments, a single solenoid actuator can be provided above each cilium and, under CPU control, the solenoids can be sequentially energized to deflect the cilia into the wells of the sample tray. According to various embodiments, a coil mechanism along the circumference and length of the cilia can provide the desired deflection. The coil mechanism can be covered by an outer tube. A controller connected to the coil mechanism can be connected to the CPU for individual control of each cilium for deflection into a desired well. Such a cilia and method manufacturing is described at JP2000233027A.

All publications and patent applications referred to herein are hereby incorporated by reference to the same extent as if each individual publication or patent application was specifically and individually indicated to be incorporated by reference.

As used herein, the word "include" and its variants are intended to be non-limiting, such that recitation of items in a list is not to the exclusion of other like items that may also be useful to the present teachings.

For the purposes of this specification and appended claims, unless otherwise indicated, all numbers expressing quantities, percentages or proportions, and other numerical values used in the specification and claims, are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges subsumed therein. For example, a range of "less than 10" includes any and all subranges between (and including) the minimum value of zero and the maximum value of 10, that is, any and all subranges having a minimum value of equal to or greater than zero and a maximum value of equal to or less than 10, e.g., 1 to 5.

It is noted that, as used in this specification and the appended claims, the singular forms "a," "an," and "the," include plural referents unless expressly and unequivocally limited to one referent. Thus, for example, reference to "a tray" includes two or more different trays. As used herein, the term "include" and its grammatical variants are intended to be non-limiting, such that recitation of items in a list is not to the exclusion of other like items that can be substituted or added to the listed items.

It will be apparent to those skilled in the art that various modifications and variations can be made to various embodiments described herein without departing from the spirit or scope of the present teachings. Thus, it is intended that the various embodiments described herein cover other modifications and variations within the scope of the appended claims and their equivalents.

What is claimed is:

1. A channel device comprising:
   a substrate comprising a plurality of channels for electrophoretic separation; and
   a plurality of deflectable cilia in fluid communication with the plurality of channels, wherein the deflectable cilia are adapted to loading the plurality of channels from a multi-well tray and wherein the cilia have a pitch such that adjacent cilia cannot deflect into adjacent wells of the multi-well tray.

2. The channel device of claim 1, wherein the deflectable cilia are adapted for deflection by a support.

3. The channel device of claim 1, wherein the deflectable cilia are adapted for deflection by an active mechanism.

4. The channel device of claim 1, wherein the substrate comprises a detection zone.

5. A system for electrophoretic separation comprising:
   a channel device comprising a substrate comprising a plurality of channels and a plurality of deflectable cilia in fluid communication with the plurality of channels;

a multi-well tray, wherein the cilia have a pitch such that adjacent cilia cannot deflect into adjacent wells of the multi-well tray; and a support adapted to deflect sets of the cilia to load the channels from different rows of wells of the multi-well tray.

6. The system of claim 5, further comprising a controller adapted to position at least one of the channel device, the multi-well tray, and the support.

7. The system of claim 6, further comprising a CPU adapted to direct the controller.

8. The system of claim 7, further comprising a detector adapted to collect electrophoretic separation information at a detection zone on the channel device.

9. The system of claim 8, wherein the detector is in electrical communication with the CPU to correlate loading information from the controller and electrophoretic separation information from the detector.

10. The system of claim 5, further comprising a buffer tray, wherein the support is adapted to deflect each of the cilia into the buffer tray.

11. A loading mechanism for a channel device comprising:
a plurality of deflectable cilia adapted to fluidly communicate with a plurality of channels in a substrate for electrophoretic separation, wherein the deflectable cilia are adapted to loading the plurality of channels from a multi-well tray, and wherein the cilia have a pitch such that adjacent cilia cannot deflect into adjacent wells of the multi-well tray; and
a support adapted to deflect sets of the cilia to load the channels from different rows of wells of the multi-well tray.

12. The loading mechanism of claim 11, wherein the support comprises of posts to deflect individual cilia.

13. The loading mechanism of claim 12, wherein the posts are configured such that the support can load from a row of the multi-well tray with each deflection.

14. The loading mechanism of claim 12, wherein the channels are configured such that the support can load from a row of the multi-well tray with each deflection.

15. The loading mechanism of claim 12, wherein each well in the multi-well tray corresponds to a different channel in the channel device.

16. The loading mechanism of claim 11, wherein the cilia comprise an active mechanism to control the deflection.

17. The loading mechanism of claim 11, wherein the cilia are deformable.

18. A loading mechanism for a channel device comprising:
a plurality of deflectable cilia adapted to fluidly communicate with a plurality of channels in a substrate for electrophoretic separation, wherein the deflectable cilia are adapted to loading the plurality of channels from a multi-well tray; and
a support adapted to deflect the cilia to load the channels from the multi-well tray,
wherein the cilia comprise a shape-memory alloy adapted to provide resilience to return the cilia to an initial position after the deflection.

19. A loading mechanism for a channel device comprising:
a plurality of deflectable cilia adapted to fluidly communicate with a plurality of channels in a substrate for electrophoretic separation, wherein the deflectable cilia are adapted to loading the plurality of channels from a multi-well tray; and
a support adapted to deflect the cilia to load the channels from the multi-well tray,
wherein the cilia comprise a tendon element to control the deflection.

20. A method for loading a channel device comprising:
providing a multi-well tray; and
deflecting a set of cilia from plurality of cilia into a row of wells of the multi-well tray, wherein the cilia are adapted to fluidly communicate with a plurality of channels in the channel device, and wherein the cilia have a pitch such that adjacent cilia cannot deflect into adjacent wells of the multi-well tray.

21. The method of claim 20, wherein deflecting comprises positioning a support to deflect at least one cilium.

22. A method for loading a channel device comprising:
providing a multi-well tray; and
deflecting at least one cilium from plurality of cilia adapted to fluidly communicate with a plurality of channels in the channel device, wherein deflecting comprises positioning a support to deflect at least one cilium; and
positioning at least one of the channel device and the multi-well tray to align the cilia to posts connected to the support.

23. The method of claim 22, further comprising loading sample from the multi-well tray into the channels.

24. A method for electrophoretic separation comprising:
providing a channel device comprising a substrate comprising a plurality of channels and a plurality of deflectable cilia in fluid communication with the plurality of channels;
providing a multi-well tray, wherein the cilia have a pitch such that adjacent cilia cannot deflect into adjacent wells of the multi-well tray;
providing a loading mechanism to deflect a set of the cilia to load the channels from different rows of wells of the multi-well tray;
deflecting at least one cilium to load at least one sample from the multi-well tray;
deflecting the plurality of cilia into a buffer tray; and
providing electric current for the electrophoretic separation.

25. The method of claim 24, further comprising loading the channel device.

26. The method of claim 25, wherein loading comprises positioning at least one of the channel device and the multi-well plate.

27. The method of claim 24, further comprising detecting electrophoretic separation information from a detection zone on the channel device.

* * * * *